United States Patent [19]
Wexler et al.

[11] 3,943,938
[45] Mar. 16, 1976

[54] ANAL SPHINCTER DEVICE AND BARIUM ENEMA PLUG

[76] Inventors: Paul Wexler, 110-45 Queens Blvd., New York, N.Y. 11375; Boguslav H. Fischer, 251 E. 32nd St., New York, N.Y. 10016

[22] Filed: Feb. 27, 1974

[21] Appl. No.: 446,280

[52] U.S. Cl. .................. 128/421; 128/2 A; 128/407
[51] Int. Cl.² ........................................... A61N 1/36
[58] Field of Search ........ 128/404, 407, 408, 419 R, 128/421 PE, 422, 423, 2 A

[56] References Cited
UNITED STATES PATENTS

| | | | |
|---|---|---|---|
| 3,521,641 | 7/1970 | Farensbach | 128/422 |
| 3,543,744 | 12/1970 | LePar | 128/2 A |
| 3,557,796 | 1/1971 | Keller, Jr. | 128/419 PG |
| 3,563,247 | 2/1971 | Bowers | 128/422 |
| 3,575,160 | 4/1971 | Vass et al. | 128/2 A |
| 3,648,708 | 3/1972 | Haeri | 128/422 |
| 3,727,616 | 4/1973 | Lenzkes | 128/422 |
| 3,800,800 | 4/1974 | Garbe et al. | 128/421 |

FOREIGN PATENTS OR APPLICATIONS

| | | | |
|---|---|---|---|
| 1,026,869 | 4/1966 | United Kingdom | 128/423 |
| 1,145,749 | 3/1969 | United Kingdom | 128/407 |

*Primary Examiner*—William E. Kamm
*Attorney, Agent, or Firm*—Lilling & Siegel

[57] ABSTRACT

An apparatus for stimulating the anal sphincter is provided in order to maintain the anal sphincter in a substantially continuously contracted condition. The apparatus includes a plug which is inserted in the anus such that a portion of the plug is surrounded by the anal sphincter. Electrodes are mounted on the plug in contact with anal sphincter and a signal generator generates a biphasic output signal having a positive pulse portion, a negative pulse portion and a zero output portion. The output signal is applied to the anal sphincter through the electrodes, thus causing the anal sphincter to contract and remain in a substantially contracted condition. The signal generator comprises a timer circuit which is used to operate a counter and an output driver which is controlled by the counter. The output signal from the output driver is applied to the anal sphincter through the electrodes. The plug comprises a suppository member which has an enlarged forward portion, a narrower central portion and an enlarged rear portion. The device may be used in conjunction with a barium enema to maintain the anal sphincter in a substantially contracted condition during barium enema examinations. In this arrangement, the plug has a channel which passes through the center along the axis thereof. The contrast material is then passed through this channel into the rectum and colon. The contrast material is held in the body because of the maintained contraction of the anal sphincter.

13 Claims, 10 Drawing Figures

ANAL SPHINCTER DEVICE AND BARIUM ENEMA PLUG

BACKGROUND OF THE INVENTION

1. Field of the Invention

This invention relates to an apparatus for holding the anal sphincter in a substantially continually contracted condition and more particularly to an apparatus for applying an electrical signal to the anal sphincter to stimulate the anal sphincter such that it is maintained in a substantially contracted position.

2. Description of the Prior Art

Devices have been developed for applying an electrical signal to the anal sphincter in order to contract this muscle and hold it in a substantially contracted condition. One such device is disclosed in U.S. Pat. No. 3,650,275. In devices of this type, a square wave signal at a frequency between 18 and 90 Hz is applied to the anal sphincter. Each cycle of the square wave signal consists of a positive pulse portion followed by a negative pulse portion wherein the amplitude of the positive and negative portions are the same. The square wave signal does not have a zero output portion but rather instantaneously passes through zero when switching from the positive to negative portion. The signal applied to the anal sphincter, however, has a number of disadvantages. At a given constant current, pain or discomfort is a result of the frequency of the signal. It has been found that frequencies below 100 Hz may cause great discomfort. The signal applied to the anal sphincter by this device has a further disadvantage in that it provides no period for relaxation of the anal sphincter. Since the wave shape of the output is a square wave, it is either positive or negative at all times and has no period of zero output. The anal sphincter is thus constantly being stimulated with either the positive or negative portion of the signal and there is no time for the muscle to relax. Thus a signal of this type may cause great fatigue to the anal sphincter.

One of the problems resulting from anal muscle weakness, that is, the inability of the anal sphincter to maintain a substantially contracted condition, is that it is not possible to give patients having this problem a barium enema examination. As is readily apparent, in order to give a barium enema examination, the patient's anal sphincter must be capable of contracting and holding itself in the substantially contracted condition in order to keep the contrast fluid in the rectum and colon. No successful techniques have been developed in the prior art for giving barium enema examinations to patients suffering from anal incontinence.

SUMMARY OF THE INVENTION

It is the primary object of this invention to provide an apparatus for maintaining the anal sphincter in a substantially continuously contracted condition.

It is another object of this invention to provide an apparatus for applying an electric current to the anal sphincter such that the anal sphincter is stimulated into a substantially continuously contracted condition.

It is still another object of this invention to stimulate the anal sphincter into a substantially continuously contracted condition by application of a biphasic output signal having a positive pulse portion, a negative pulse portion and a zero output portion, the zero output portion providing a rest period for the anal sphincter and thus reducing fatigue.

It is still another object of this invention to provide an apparatus for stimulating the anal sphincter wherein the apparatus includes a plug member having electrodes thereon which contact the anal sphincter and a signal generator means comprising a timer, counter, and output driver for applying an electrical signal to the electrodes thereby stimulating the anal sphincter.

It is still a further object of this invention to provide an apparatus for stimulating the anal sphincter to maintain it in a substantially contracted condition during a barium enema examination which includes a plug having a channel through the center along the axis thereof wherein a barium enema is coupled to the channel and contrast fluid flows through the channel into the rectum and colon.

This invention provides an apparatus for stimulating the anal sphincter to maintain it in a substantially continuously contracted condition. The apparatus comprises a plug or suppository member which is inserted into the anus such that a portion of the suppository member is surrounded by the anal sphincter. Electrodes are mounted on the suppository member such that the electrodes contact the anal sphincter. A signal generator means including a timer circuit, two-stage counter and output driver is used to generate a biphasic output signal having a positive pulse portion, a negative pulse portion and a zero output portion. This signal is applied to the anal sphincter through the electrodes, and stimulates the anal sphincter such that it is held in a substantially continuously contracted condition for the duration of the application of the signal.

The zero output portion provides a rest period for the anal sphincter. Fatigue of this muscle is thereby reduced. The discomfort of the patient is also greatly reduced once the frequency of the signal is raised above 100 Hz, for example, to a frequency of approximately 300 Hz. In the present invention, it has been found that patient comfort, and therefore, an increase in the ability of the anal sphincter muscle to contract, is achieved with frequencies between 300 Hz–2000 Hz at any given constant voltage or current. In the preferred embodiment of the invention, optimum results are achieved with frequencies between 300 Hz and 1000 Hz.

DETAILED DESCRIPTION OF THE PREFERRED EMBODIMENTS

Figure 1A:
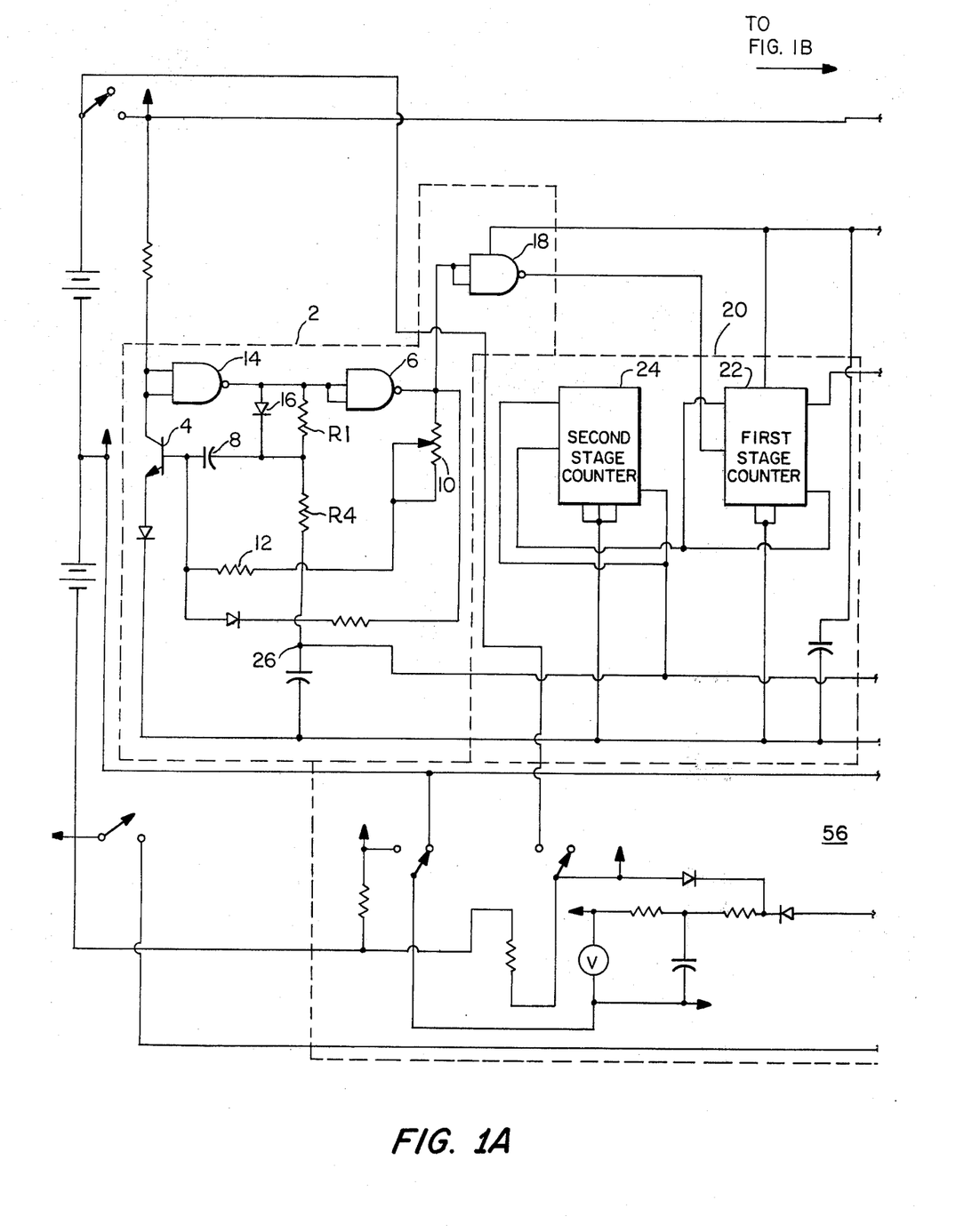
FIGS. 1A and 1B are a schematic circuit diagram of the signal generator of the present invention.
Figure 1B:
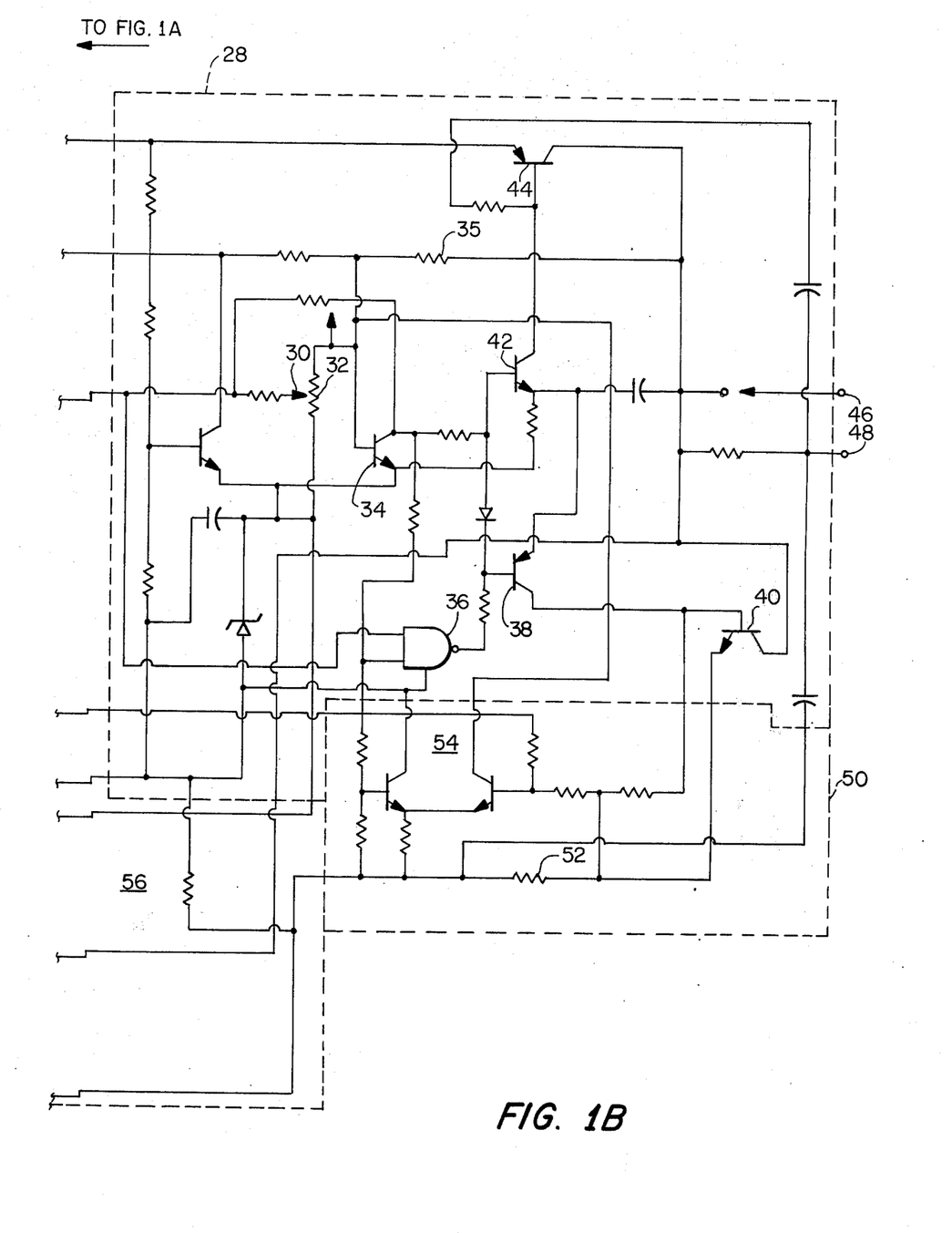

The present invention is directed to an apparatus for stimulating the anal sphincter to maintain the sphincter in a substantially continuously contracted condition. FIG. 1 illustrates a signal generator for generating a biphasic output signal having a positive pulse portion, a negative pulse portion, and a zero output portion. This signal is applied to the anal sphincter in order to maintain it in the substantially continuously contracted condition but allowing for a rest period for the anal sphincter to avoid muscle fatigue. Referring to FIG. 1, astable multivibrator 2 generates a series of timing pulses at gate 6 such as that illustrated in FIG. 2A. Initially, transistor 4 is off and gate 6 has an output which is high. The high output of gate 6 charges the capacitor 8 through resistors 10 and 12 until the charge on capacitor 8 is sufficient to turn on transistor 4. When transistor 4 turns on, gate 14 goes high and gate 6 goes low. Capacitor 8 then rapidly discharges through gate 14 and diode 16. After discharge, the multivibrator circuit is ready to begin another cycle. The output of gate 18 is applied to two-stage counter 20. The gates 6, 14 and 18 may, for example, be RCA COS/MOS digital integrated circuits of the QUAD NAND type.

Two-stage counter 20 comprises two identical stages which may, for example, be RCA COS/MOS digital integrated circuits of the dual flip-flop type. First and second stages 22 and 24 of the counter are interconnected such that when the output of gate 18 is applied to the input of stage 22, the output of stage 22 corresponds to FIG. 2B and the output of stage 24 corresponds to FIG. 2C.

Figure 2A:
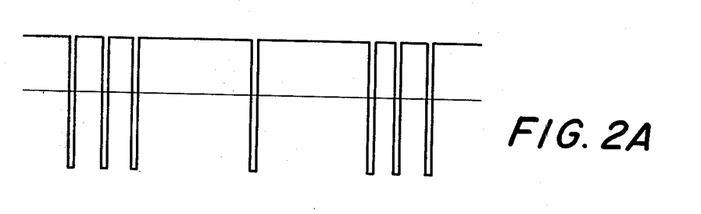
FIGS. 2A–2D illustrate the wave forms at various points in the signal generator of the present invention.

The output of stage 24 is fed back to the astable multivibrator 2, thus the voltage at point 26 varies in accordance with the output of stage 24. This variation causes a corresponding variation in the current through R1 and R4 and thus changes the period of the astable multivibrator 2. The feedback of the output of the counter to the astable multivibrator thus causes the change in the period of the timing pulses which is illustrated in FIG. 2A of the drawings.

The output of the counter 20 is applied to output driver circuit 28. The output of stage 22 of the counter 20 is supplied to output driver 28 through tap 30 of a voltage divider circuit comprising resistors 32 and 35. The voltage divider circuit controls the voltage supply to the base of the transistor 34. The output of stage 22 is also applied to one input of gate 36 which is of the same type as gates 6, 14 and 18. The other input of gate 36 is coupled to the output of stage 24 of counter 20.

Output driver circuit 28 produces an output signal which is biphasic, i.e., has an average voltage out equal to zero and which comprises three portions, a first portion being a positive going pulse, a second portion being a negative going pulse and a third portion being zero.

The wave shape of the output signal is extremely important for proper stimulation of the anal sphincter. The biphasic characteristic of the signal prevents tissue damage to the muscle tissue while the zero output portion of the signal provides a rest period for the muscle thus eliminating muscle fatigue. The optimum frequency range for the signal is 200–600 Hz. Stimulation in this range minimizes the pain caused by the application of an electrical signal.

Figure 2B:
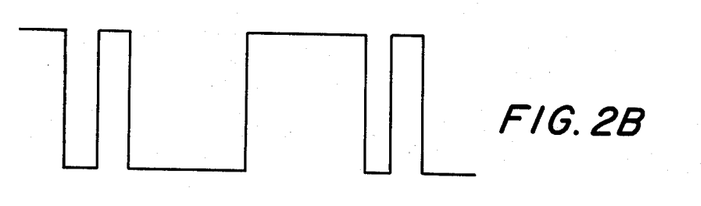
Figure 2C:
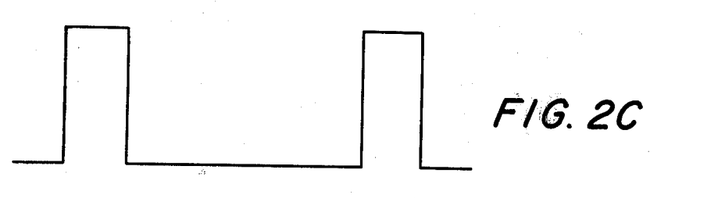
Figure 2D:
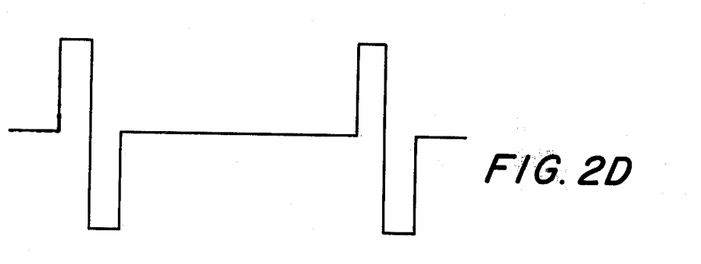

As indicated above, the output of the output driver circuit is controlled by the output of the stages of the two-stage counter 20. When the output of stage 22 is low and the output of stage 24 is high, the output of the driver circuit is a positive pulse. When the output of stage 22 is high and the output of stage 24 is high, the output of the driver circuit is a negative pulse. When the output of stages 22 and 24 are both low, the output of the driver circuit is zero. The relationship between the outputs of the stages of the counter and the output of the driver circuit is illustrated in FIGS. 2B, 2C and 2D.

In particular, when the output of stage 22 is low, and the output of stage 24 is high, the output of gate 36 is high because of the application of the low output of stage 22 to the input of gate 36. The high output on gate 36 turns off transistor 38 and thereby transistor 40. The positive pulse output is produced by the operation of transistors 34, 42 and 44. The output is self-regulated by means of resistor 35 which feeds back the output to the base of transistor 34, causing the output of the apparatus to decrease in response to an increase in the output and to increase in response to a decrease, thus regulating the output.

When the output of stages 22 and 24 are both high, both inputs to gate 36 are high, thus producing a low output. This low output turns on transistors 38 and 40 and turns off transistors 42 and 44. A negative output pulse is produced by means of transistors 34, 38 and 40. The output during the negative going pulse portion is also regulated by means of feedback resistor 35, in the same manner as in the positive going output pulse.

When the output of counter stages 22 and 24 are both low, transistors 38 and 40 and 42 and 44 are all turned off, thus producing a zero output. The output signal from the output driver circuit is applied to terminals 46 and 48. Leads (not shown) extend from terminals 46 and 48 to the electrodes, mounted on the plug, which are in contact with the anal sphincter.

Current limiter circuit 50 is coupled to the output of the driver circuit 28 for limiting the current applied to the anal sphincter through the electrodes. This is necessary in order to prevent damage to the tissue of the anal sphincter due to an excessive amount of current. Current limiter 50 includes a sensing resistor 52 which is coupled to differential circuit 54. The output of the differential circuit 54 is applied to the base of transistor 34, thus controlling the output of the device.

Meter circuit 56 may be included in order to detect the peak positive output of the apparatus. This is used to monitor the peak voltage applied to the anal sphincter.

The voltage level of the output, which has the same magnitude in the positive and negative pulse portions, may be controlled by the adjustment of tap 30 of variable resistor 32. Thus, the voltage applied to the anal sphincter would depend on the particular condition of the patient.

It is noted that the values of the capacitor 8 and the resistors R1, R4 and 12 are selected so that any frequency can be achieved, for example, between the range of about 300 Hz to about 2000 Hz. Also, the pulse width is in a like manner determined by such range. In this connection, the variable resistor or trim pot 10 is employed to set the predetermined period of the astable multivibrator, thus setting the frequency of the output to the predetermined value.

It will also be appreciated that although the trim pot 10 is optional in the circuitry, it permits the use of more economical electrical components.

The frequency of the apparatus of the invention is set at a value which has been found to optimize the reaction of the anal sphincter and minimize pain and/or discomfort to the patient. It appears that lower frequencies tend to generate more pain than higher frequencies, and they generate stronger contractions of the anal sphincter. For example, frequencies of about 300 Hz and above have been successfully employed in the practice of the invention; and it is suggested that a frequency as high as 2000 Hz will also achieve satisfactory test results. The preferred range is between 300 Hz and 1000 Hz.

Referring now to FIGS. 3-6 of the drawings, a plug constructed in accordance with the principles of the present invention is partially inserted into the anus and has an enlarged forward end to prevent its being forced out of the anus by contraction of the anal sphincter. A narrow central portion is surrounded by the anal sphincter when it contracts and an enlarged rear end prevents it from being completely inserted into the rectum. The shape of the plug is important in order to achieve optimum results and, from the foregoing, it will be understood that the configuration of the plug conforms strictly to the physiological contour of the anal canal. This is achieved by taking plaster of paris casts of the canal. A cadaver may be used for this purpose, though it is possible to use a living person, for example, a paraplegic.

It has been found that optimum results are achieved when the central portion or neck of the plug is dimensioned between 6 mm. and 10 mm. The enlarged forward end which is partially inserted into the anus is dimensioned between 20 mm.-27 mm., and the rear end is dimensioned between 16 mm. and 22 mm. All of these dimensions are measured axially of the plug.

The central portion or neck separates a pair of concentrically disposed electrodes which are dimensioned between 6 mm. and 9 mm. in an axial direction. While the length of the neck portion of the plug can be between 6 mm. and 10 mm., the spacing between the electrodes should be between 8 mm. and 10 mm., so that they will make electrical contact with the anal sphincter.

The electrodes are fixed to the plug. This may be accomplished in a number of different ways considered apparent to anyone skilled in the art to which the invention pertains. It is to be remembered, however, that the outer surface of the electrodes should be flush with the outer surface of the plug to provide a smooth overall contour of the plug. The electrodes may, therefore, be recessed into the surface of the plug. Within this context, one possibility contemplates winding wire about the plug and in the recesses provided for the electrodes. The electrodes may also be fabricated of a unitary piece of metal which are then fixed within the recesses at the surface of the plug in any suitable manner.

The plug should preferably be disposable. Economy of manufacture is, therefore, important, and it is thus further contemplated that a simple piece of tin foil may suffice for the electrodes. In this example, it may not be necessary to provide recesses in the surface of the plug.

The plug may be machined, or it may be molded. Again, the life of the plug is to be considered. If it is to be disposable, one manufacturing process may be dictated. If it is to be re-usable, through a suitable sterilization process, another manufacturing process may be chosen.

Figure 3:
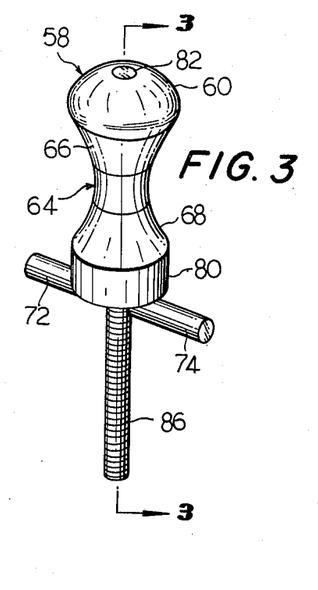
FIG. 3 is a perspective view of a barium enema plug constructed in accordance with the principles of the present invention.
Figure 4:
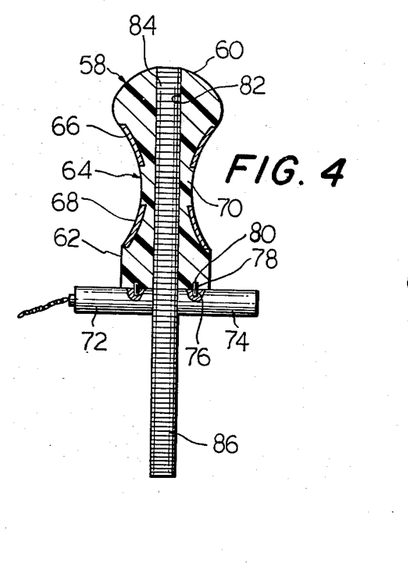
FIG. 4 is a cross-sectional view of the plug of FIG. 3 taken along the lines 3—3 of that figure.

A plug 58, constructed in accordance with the principles of the present invention, and particularly adapted to be used for diagnostic barium enema examination, is illustrated in FIGS. 3 and 4. The plug 58 comprises an enlarged forward end 60 separated from an enlarged rear end 62 by a neck portion 64. The front portion or forward end 60 prevents the plug from being forced out of the anus by contraction of the anal sphincter, while the rear end 62 prevents complete insertion of the plug into the rectum.

The narrow central or neck portion 64 is adapted to be surrounded by the anal sphincter when it contracts.

The plug 58 further comprises a pair of electrodes 66 and 68. The electrodes are fixed to the plug at or close to the narrow central or neck portion 64, so that the electrodes make electrical contact with the anal sphincter. The electrodes are separated by an isolating portion 70. This portion is actually comprised of the narrowest part of the neck portion 64. The isolating portion 70 is preferably of 8 mm. to 10 mm. in length, that is, in a direction extending longitudinally or axially of the plug 58, and the electrodes preferably are between 6 mm. and 9 mm. in length, all as previously pointed out.

Though not shown, it will be understood that leads are coupled to the electrodes 66 and 68, and apply the output signal from the signal generating circuit to the electrodes. The leads may be connected to the electrodes in any suitable manner and, depending upon the plug 58 and its particular application, may extend from the electrodes to a location without the plug in different ways considered apparent to those skilled in the art to which the present invention pertains.

The plug 58 also comprises a pair of bars 72 and 74. These bars, in the preferred embodiment of a barium enema plug illustrated in FIGS. 3 and 4, are cylindrical. They may be affixed to the enlarged rear end 62 of the plug 58 in any suitable manner. One method of attachment is illustrated in the drawings, and comprises drilling or otherwise providing a small bore 76 in each of the bars 72 and 74, and a complementary bore 78 in the rear end 62 of the plug. A dowel-like member 80 may then be used together with, for example, a suitable epoxy cement to insure that the bars 72 and 74 are fixed to the plug 58.

The bars 72 and 74 are adapted to prevent internal displacement of the plug 58, which might otherwise occur as a result of contraction of the external sphincter muscle during electrical stimulation. To this end, the bars 72 and 74 are adapted to be positioned against the body between the buttocks after insertion of the plug 58. In this position, the bars extend in a direction generally longitudinally of the body.

Since the plug 58 is particularly adapted to be used for diagnostic barium enema examination, it comprises, in addition, a channel 82. The channel extends the full length of the plug, from the enlarged front end 60 to the enlarged rear end 62. The channel 82 is particularly adapted to fixedly receive a tube 84 which is longer than the plug 58, and therefore extends outwardly of the plug at the rear end 62 thereof. The tube 84 may be secured to the plug 58 within the channel 82 in any suitable manner, as, for example, by means of a suitable cement. The portion of the tube extending outwardly of the plug is particularly adapted to function as a connecting nipple, enabling the plug to be connected to a barium enema reservoir by means of tubing (not shown) or in any other suitable manner. To this end, the external surface of the tube 84 may be provided with striations or score lines 86.

Figure 5:
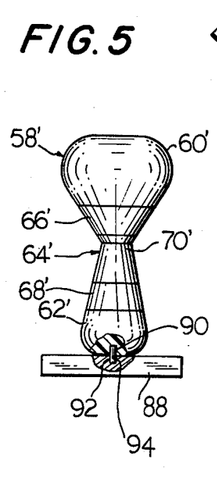
FIG. 5 is a plug constructed in accordance with the principles of the present invention and used for fecal incontinence.

FIG. 5 illustrates a plug that is particularly adapted to control fecal incontinence. The parts of the plug illustrated in this figure that are similar to the parts of the plug 58 illustrated in FIGS. 3 and 4 are identified by like reference characters. These reference characters, however, are primed.

The plug 58' comprises an enlarged forward end 60' and an enlarged rear end 62' separated by a central or neck portion 64'. The plug 58' comprises, further, electrodes 66' and 68' separated by an isolating portion 70'.

Since the plug 58' is particularly adapted to control fecal incontinence, it is solidly built, as is clearly illustrated in FIG. 5. The plug 58' comprises, further, a unitary, one-piece horizontal bar 88. This bar performs the same function as the bars 72 and 74 of the plug 58, and may be affixed to the plug 58' at the enlarged rear end 62' thereof in any suitable manner. In the preferred embodiment of this form of the invention, as illustrated in FIG. 5, a small bore 90 is drilled into the enlarged rear end 62'. A bore 92 is drilled through the bar 88, and is adapted to be disposed in alignment with the bore 92. A dowel-like member 94 may then be used to fixedly secure the bar 88 to the enlarged rear end 62' and, in this connection, a suitable cement, such as an epoxy, is used. In this embodiment, the bar 88 may be of a unitary one-piece construction because there is no tubing, such as the tube 84 in the embodiment of FIGS. 3 and 4, extending outwardly of the plug 58' at the rear end 62' thereof.

In this embodiment, just as in the embodiment illustrated in FIGS. 3 and 4, leads (not shown) are adapted to be connected or coupled to the electrodes 66' and 68' in any suitable manner, and will extend outwardly of the plug 58' so that the output signal from the signal generating circuit can be applied to the electrodes.

Figure 6:
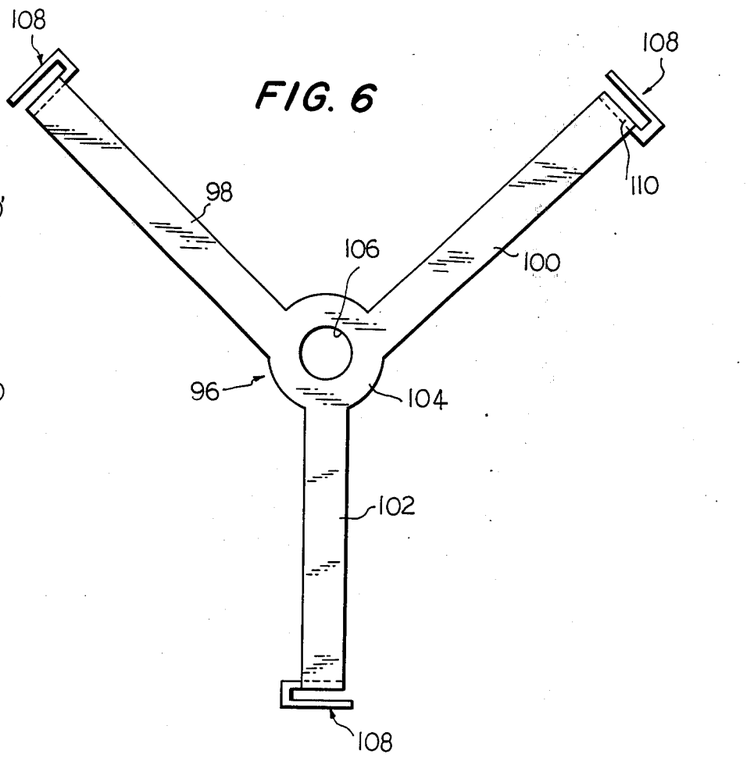
FIG. 6 is a retainer strap arrangement for use with the plug of FIGS. 3 and 4.

Returning now to FIGS. 3 and 4 of the drawings, and referring also to FIG. 6, it will be understood that when a plug constructed in accordance with the principles of the present invention is used for diagnostic barium enema examination, the contrast material is injected into the rectum and colon by passage through the channel or tube extending through the plug. During and after the injection of the contrast fluid, the anal sphincter is maintained in a substantially contracted condition by application of the output signal of the signal generator circuit to the anal sphincter through the electrodes on the plug. Thus, after insertion of the plug 58 in the anal canal, and during any diagnostic barium enema examination, where the contrast fluid is injected into the body through the channel 82 and the tube 84, it is desirable to be able to secure the plug to the body. To this end, a securing means 96 (FIG. 6) comprises three straps 98, 100 and 102. The angle between the straps 98 and 100 is preferably 90°, whereas the angle between each of the straps 98 and 100, on the one hand, and the strap 102, on the other, is 135°.

The straps may be fabricated of any suitable material, such as plastic, and may be structurally associated with one another where they intersect in any suitable manner. In the embodiment illustrated in FIG. 6, the straps 98, 100 and 102 are positioned in overlapping relationship with respect to one another. This overlapping relationship provides a mass of plastic 104. An aperture 106 is provided generally centrally of the mass of plastic. This may be accomplished, for example, by puncturing a hole through the plastic. The diameter of the aperture 106 should be of sufficient dimension to enable the tube 84 to be inserted therethrough. The three straps may then be moved along the tube until the mass of plastic 104 is in position substantially against the bars 72 and 74.

Another method of structurally associating the three straps with one another is to provide a washer (not shown). The three straps may be affixed to the washer in any suitable manner, for example, by riveting or by use of a suitable cement. The washer will comprise an aperture of sufficient diameter enabling the tube 84 to extend therethrough.

The securing means 96 is instrumental in maintaining proper alignment of the plug 58 along the axis of the anal canal, and also prevents expulsion of the plug by gravitational forces of the heavy weight contrast material. To accomplish this, the straps are affixed to the body. If the position of the body is envisioned as being upon its back, the straps 98 and 100 are positioned upon the legs by moving them through the area of the groin. The strap 102 is positioned at the back by moving it rearwardly and along the buttocks. The straps may be affixed to the body in any suitable manner, as, for example, by using adhesives. Another possibility is to provide a belt (not shown) which may be disposed about the waist or hips of the body. The belt and the straps may be provided with Velcro portions (also not shown) so that the straps may be removably connected to the belt. And, in yet another embodiment, as illustrated in FIG. 6, the straps may be provided with fastening hooks 108. When the fastening hooks are used, the ends of the straps 98, 100 and 102 will have to be doubled over to provide loops 110 at their end. Corresponding loops on the belt will also have to be provided.

It should now be readily apparent that a plug constructed in accordance with the principles of the present invention, for example, the plugs 58 and 58', may be any one of a number of shapes. The primary requirement is that the plug must have an enlarged forward end, a narrow central portion or neck and an enlarged rear end. The contour of the plug, and the dimensions of its various portions, must be chosen so that the plug will structurally conform to the physiological contour of the anal canal. The electrodes can be mounted anywhere on the plug as long as they contact the anal sphincter. The width of the electrodes, that is, their length in a direction axially of the plug, must be a minimum of 6 mm. in order to insure proper contact with the mucous membranes of the anal canal. The electrodes are spaced from one another by an isolating portion at the neck of the plug, and the width or length of this portion should be between 8 mm. and 10 mm.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. An apparatus for stimulating the anal sphincter to maintain it in a continuously substantially contracted condition while a fluid is being introduced into the rectum, said apparatus comprising:
   a. plug means for insertion into the anus such that a portion of said plug means is surrounded by the anal sphincter, said plug means having a central aperture therethrough for the introduction of fluid into the rectum when said plug means is inserted into the anus;
b. electrode means mounted on said plug means such that said electrode means contacts the anal sphincter when said plug means is inserted into the anus, said electrode means being adapted to apply an output signal to the anal sphincter to cause it to contract when fluid is introduced into the rectum through said central aperture in said plug means, said output signal being derived from an external signal generator means; and
c. said external signal generator means generating a biphasic output signal having a positive pulse portion, a negative pulse portion and a zero output portion, said external signal generator means being coupled to said electrode means such that said output signal is applied to the anal sphincter through said electrode means, said output signal having a frequency greater than or equal to 300 Hz. and less than or equal to 1000 Hz.

2. An apparatus for stimulating the anal sphincter to maintain the anal sphincter in a continuously substantially contracted condition, said apparatus comprising:
plug means for insertion into the anus such that a portion of said plug means is surrounded by the anal sphincter,
electrodes mounted on said plug means wherein said electrodes contact the anal sphincter,
signal generator means for generating a biphasic output signal having a positive pulse portion, a negative pulse portion, and a zero output portion, said signal generating means being coupled to said electrodes such that said output signal is applied to the anal sphincter through said electrodes, whereby the application of said output signal to the anal sphincter causes the anal sphincter to contract and remain in a contracted condition,
said signal generator means comprising timer means for generating a plurality of timing pulses, counter means coupled to said timer means for counting said timing pulses and for producing an output in accordance with the number of pulses counted, and output driver means coupled to said counter means for producing said output signal and for applying said output signal to said electrodes,
said counter means comprising a two stage counter and means for simultaneously applying the output of each stage to said output driver means for controlling said output driver means, and means for creating a feedback output from one of the counter stages to said timer means for changing the period of said timer means.

3. The apparatus of claim 2 wherein said plug means has a central aperture therethrough for the introduction of fluid into the rectum when said plug means is inserted into the anus.

4. The apparatus of claim 3 wherein a tube is mounted within said central aperture of said plug means, said tube having a rear end portion extending rearwardly of said plug means and being adapted to be connected to an enema reservoir.

5. The apparatus of claim 3 wherein the frequency of said output signal is at least 100 Hz.

6. The apparatus of claim 5 wherein the frequency of said output signal equals or is less than 2000 Hz.

7. The apparatus of claim 6 wherein the frequency of said output signal equals or is greater than 300 Hz.

8. The apparatus of claim 5 wherein the frequency of said output signal equals or is greater than 300 Hz.

9. The apparatus of claim 8 wherein the frequency of said output signal equals or is less than 1000 Hz.

10. An apparatus for stimulating the anal sphincter to maintain it in a continuously substantially contracted condition while a fluid is being introduced into the rectum, said apparatus comprising:
a. plug means for insertion into the anus such that a portion of said plug means is surrounded by the anal sphincter, said plug means having a central aperture therethrough for the introduction of fluid into the rectum when said plug means is inserted into the anus;
b. electrode means mounted on said plug means such that said electrode means contacts the anal sphincter when said plug means is inserted into the anus, said electrode means being adapted to apply an output signal to the anal sphincter to cause it to contract when fluid is introduced into the rectum through said central aperture in said plug means; and
c. a signal generator means for generating a biphasic output signal having a positive pulse portion, a negative pulse portion, and a zero output portion, said signal generator means being coupled to said electrodes such that said output signal is applied to the anal sphincter through said electrodes, said signal generator means having a timer means for generating a plurality of timing pulses, a counter means, coupled to said timer means, for counting said timing pulses and for producing an output in accordance with the number of pulses counted and an output driver means, coupled to said counter means for producing said output signal and for applying said output signal to said electrodes, said output driver means including voltage regulation means for regulating the magnitude of the positive and negative pulse portions of the output signal.

11. The apparatus of claim 10 wherein said output driver means further includes current limiter means for limiting the magnitude of the current of said output signal.

12. An apparatus for stimulating the anal sphincter to maintain it in a continuously substantially contracted condition while a fluid is being introduced into the rectum, said apparatus comprising:
a. plug means for insertion into the anus such that a portion of said plug means is surrounded by the anal sphincter, said plug means having a central aperture therethrough for the introduction of fluid into the rectum when said plug means is inserted into the anus;
b. electrode means mounted on said plug means such that said electrode means contacts the anal sphincter when said plug means is inserted into the anus, said electrode means being adapted to apply an output signal to the anal sphincter to cause it to contract when fluid is introduced into the rectum through said central aperture in said plug means; and
c. a signal generator means for generating a biphasic output signal having a positive pulse portion, a negative pulse portion, and a zero output portions, said signal generator means being coupled to said electrodes such that said output signal is applied to the anal sphincter through said electrodes, said signal generator means having a timer means for generating a plurality of timing pulses, a counter means, coupled to said timer means, for counting said timing pulses and for producing an output in accordance with the number of pulses counted and an output driver means, coupled to said counter means for producing said output signal and for applying said output signal to said electrodes, said counter means having a two-stage counter and means for simultaneously applying the output of each stage to said output driver means for controlling said output driver means, and wherein means are provided to create a feedback output from one of the stages to said timer means for changing the period of said timer means.

13. An apparatus for stimulating the anal sphincter to maintain it in a continuously substantially contracted condition while a fluid is being introduced into the rectum, said apparatus comprising:
   a. plug means for insertion into the anus such that a portion of said plug means is surrounded by the anal sphincter, said plug means having a central aperture therethrough for the introduction of fluid into the rectum when said plug means is inserted into the anus;
   b. electrode means mounted on said plug means such that said electrode means contacts the anal sphincter when said plug means is inserted into the anus, said electrode means being adapted to apply an output signal to the anal sphincter to cause it to contract when fluid is introduced into the rectum through said central aperture in said plug means; and
   c. a signal generator means for generating a biphasic output signal having a positive pulse portion, a negative pulse portion, and a zero output portion, said signal generator means being coupled to said electrodes such that said output signal is applied to the anal sphincter through said electrodes, said signal generator means having a timer means for generating a plurality of timing pulses, a counter means, coupled to said timer means, for counting said timing pulses and for producing an output in accordance with the number of pulses counted, an output driver means, coupled to said counter means for producing said output signal and for applying said output signal to said electrodes, and a meter means coupled to said output driver means for detecting and indicating the peak output voltage of said output signal.

\* \* \* \* \*